(12) United States Patent
Chalifoux

(10) Patent No.: US 12,410,394 B2
(45) Date of Patent: Sep. 9, 2025

(54) COMPOSITION COMPRISING NICOTINAMIDE MONONUCLEOTIDE AND LEUCOMETHYLENE BLUE

(71) Applicant: Athergen, Inc., Dover, DE (US)

(72) Inventor: Joseph Chalifoux, Nashua, NH (US)

(73) Assignee: Athergen, Inc., Dover, DE (US)

( * ) Notice: Subject to any disclaimer, the term of this patent is extended or adjusted under 35 U.S.C. 154(b) by 0 days.

(21) Appl. No.: 18/093,860

(22) Filed: Jan. 6, 2023

(65) Prior Publication Data

US 2024/0228949 A1 Jul. 11, 2024

(51) Int. Cl.
  *C12N 5/00* (2006.01)
  *C12N 5/074* (2010.01)
  *C12N 15/86* (2006.01)

(52) U.S. Cl.
  CPC ......... *C12N 5/0018* (2013.01); *C12N 5/0607* (2013.01); *C12N 15/86* (2013.01); *C12N 2500/40* (2013.01); *C12N 2501/60* (2013.01)

(58) Field of Classification Search
  CPC .... C12N 5/0018; C12N 5/0607; C12N 15/86; C12N 2500/40; C12N 2501/60
  See application file for complete search history.

(56) References Cited

U.S. PATENT DOCUMENTS

| | | |
|---|---|---|
| 11,324,764 B2 | 5/2022 | Dischler |
| 11,344,558 B2 | 5/2022 | Wischik |
| 2011/0256175 A1* | 10/2011 | Hope ............... A61P 33/00 424/234.1 |
| 2015/0320706 A1 | 11/2015 | Imbimbo |
| 2018/0021553 A1* | 1/2018 | Wang ............... A61L 29/16 604/93.01 |
| 2018/0216076 A1* | 8/2018 | Hebrok ............ A61K 35/39 |
| 2021/0244665 A1* | 8/2021 | Fisher ............ A61K 9/1277 |

FOREIGN PATENT DOCUMENTS

| | | |
|---|---|---|
| WO | WO-2017082294 A1 * | 5/2017 |
| WO | 2021/001326 A1 | 1/2021 |
| WO | WO-2022184825 A1 * | 9/2022 |

OTHER PUBLICATIONS

Yap et al. "Deriving Insulin-Producing Cells from Trans-differentiating Adipose-Derived Mesenchymal Stem Cells." Diabetes. vol. 66. 1701 N Beauregard St, Alexandria, VA 22311-1717 USA: Amer Diabetes Assoc, 2017. (Year: 2017).*
Yoshino et al. "Nicotinamide mononucleotide increases muscle insulin sensitivity in prediabetic women." Science. Jun. 11, 2021;372(6547):1224-1229. (Year: 2021).*
Galagan et al. "Reversible photoreduction of methylene blue in acrylate media containing benzyl dimethyl ketal." Journal of Photochemistry and Photobiology A: Chemistry 195.2-3 (2008): 378-383. (Year: 2008).*
Collas et al. "On the way to reprogramming cells to pluripotency using cell-free extracts." Reprod Biomed Online. Jun. 2006;12(6):762-70. (Year: 2006).*
Kelaini et al. "Direct reprogramming of adult cells: avoiding the pluripotent state." Stem Cells Cloning. 2014; 7: 19-29. (Year: 2014).*
Qin et al. "Small molecules for reprogramming and transdifferentiation." Cellular and Molecular Life Sciences vol. 74, pp. 3553-3575 (2017) (Year: 2017).*
Hao et al. "Direct induction of functional neuronal cells from fibroblast-like cells derived from adult human retina." Stem Cell Res. Aug. 2017;23:61-72. (Year: 2017).*

* cited by examiner

*Primary Examiner* — Titilayo Moloye
(74) *Attorney, Agent, or Firm* — Greenberg Traurig, LLP; Melissa Hunter-Ensor; Nicholas R. Ballor

(57) ABSTRACT

A cell reprogramming composition and method wherein the composition includes a base molecule, β-nicotinamide mononucleotide, trichostatin A and zwitterionic liposomes and wherein the method includes receiving a cell and reprogramming agents, wherein the reprogramming agents comprise Oct-4, Sox 2 and Klf4, to reprogram the cell to an embryonic state.

10 Claims, 10 Drawing Sheets

112

116

COMPOSITION COMPRISING NICOTINAMIDE MONONUCLEOTIDE AND LEUCOMETHYLENE BLUE

FIELD OF THE INVENTION

The present invention generally relates to the field of cell reprogramming. In particular, the present invention is directed to a method and composition of cell reprogramming.

BACKGROUND

There are various known sources of aging and functional studies in model organisms and humans indicate that epigenetic changes have a huge influence on the aging process. These epigenetic changes occur at various levels, including reduced bulk levels of the core histones, altered patterns of histone posttranslational modifications and DNA methylation, replacement of canonical histones with histone variants, and altered noncoding RNA expression, during both organismal aging and replicative senescence. The result of epigenetic changes during aging is altered local accessibility to the genetic material, leading to aberrant gene expression, reactivation of transposable elements, and genomic instability. Many people believe that aging is inevitable and an effective method of cell reprogramming to reverse aging remains an elusive goal.

SUMMARY OF THE DISCLOSURE

In an aspect, a composition for reprogramming cells, wherein the composition includes a base molecule, β-nicotinamide mononucleotide, trichostatin A and zwitterionic liposomes.

In another aspect, a method of reprogramming cells, wherein the method includes receiving a cell and reprogramming agents, wherein the reprogramming agents comprise Oct-4, Sox 2, and Klf4 or Oct-4, Sox 2, and Klf4, and c-Myc to reprogram the cell to an embryonic state.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to a novel composition and method of cell reprogramming. Aspects of the present disclosure may be administered orally, injected, or by other means to a user to counter aging or to cure a disease. Countering aging may include cell rejuvenation and reducing and/or preventing plaque formations in the brain. Exemplary embodiments illustrating aspects of the present disclosure are described below in the context of several specific examples.

Figure 1:
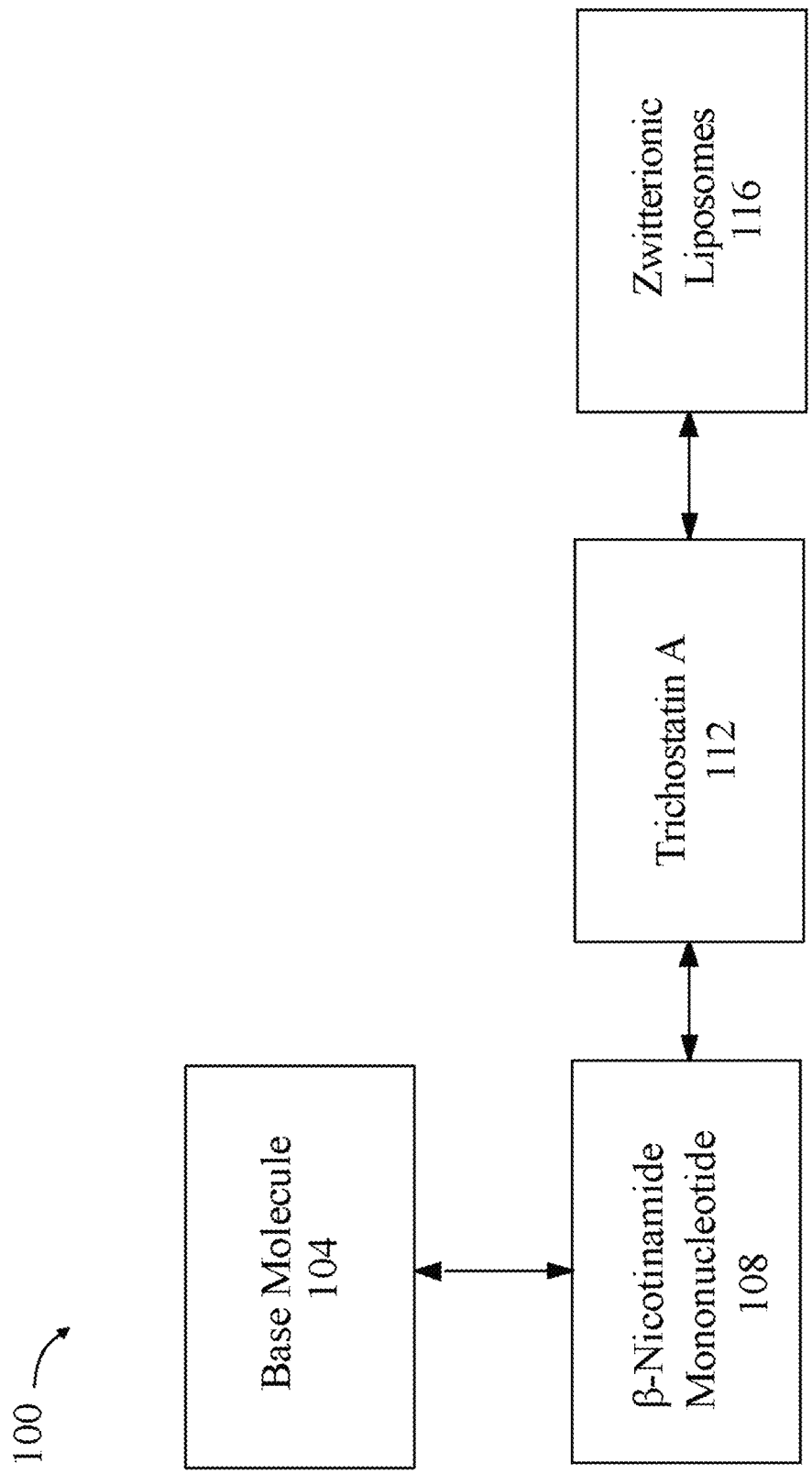
FIG. 1 is a block diagram of an exemplary embodiment of an anti-aging composition.

Referring now to FIG. 1, an exemplary embodiment of a cell reprogramming composition 100 is illustrated. A base molecule 104 is received. A "base molecule" as used in this disclosure if defined as a molecule in an aqueous solution that can accept protons or donate electrons. A base molecule of partially reduced methylene blue to leucomethylene blue may be used. "Methylene blue" as used in this disclosure is defined as an organic chloride salt having 3,7-bis (dimethylamino) phenothiazin-5-ium as the counterion. It may be commonly used as a dye that also exhibits antioxidant, antimalarial, antidepressant and cardioprotective properties. It may have a role as an EC 1.4.3.4 (monoamine oxidase) inhibitor, an acid-base indicator, a fluorochrome, an antidepressant, a cardioprotective agent, an EC 3.1.1.8 (cholinesterase) inhibitor, a histological dye, an EC 4.6.1.2 (guanylate cyclase) inhibitor, an antioxidant, an antimicrobial agent, a neuroprotective agent, a physical tracer and an antimalarial. "Leucomethylene blue" as used in this disclosure is defined as a member of the class of phenothiazines that is 10H-phenothiazine in which the ring hydrogens at positions 3 and 7 have been replaced by dimethylamino groups. It may have a role as a fluorochrome, a bacterial xenobiotic metabolite, a rat metabolite and a mouse metabolite. Leucomethylene blue may have properties of prevention and treatment to Alzheimer's disease as well as being protective against neural apoptosis and ischemia/reperfusion injury. It may even be effective as a single intravenous (IV) dose treatment at diminishing neurological deficits after traumatic brain injuries. Leucomethylene blue (LMB) may have a positive effect on prevention of Aβ/Tau deposition/aggregation and other tauopathies. Aβ stands for Amyloid β and the deposition of it in the brain may be an early and invariable feature of Alzheimer's disease. Tauopathies, including Alzheimer's disease, are a group of neuro degenerative diseases characterized by abnormal hyperphosphorylation of microtubule-associated protein Tau that leads to the formation of neurofibrillary tangles. Amyloid β is a protein fragment which is deposited in the brain in the form of sticky plaques in an increased manner in individuals with Alzheimer's disease. Methylene blue may essentially stain the plaques in the brain, thereby putting the body on notice that itis a pathogen which the body then seeks to remove. LMB may also have a positive effect on epigenetic changes. "Epigenetic changes" as used in this disclosure is defined as genetic modifications that impact gene activity without changing the DNA sequence. For example, smoking can result in epigenetic changes, at certain parts of the AHRR (aryl hydrocarbon receptor repressor) gene, smokers tend to have less DNA methylation than non-smokers. The difference is greater for heavy smokers and long-term smokers. After quitting smoking, former smokers can begin to have increased DNA methylation at this gene. LMB also easily crosses the blood brain barrier (BBB). "Blood brain barrier" as used in this disclosure is defined as is a crucial immunological feature of the human central nervous system (CNS), composed of many cell types, the BBB is both a structural and functional roadblock to microorganisms, such as bacteria, fungi, viruses or parasites, which may be circulating in the bloodstream. The blood-brain barrier (BBB) is vital for maintaining brain homeostasis by enabling an exquisite control of exchange of compounds between the blood and the brain parenchyma. Moreover, the BBB may prevent unwanted toxins and pathogens from entering the brain. This barrier, however, breaks down with age and further disruption is a hallmark of many age-related disorders. Anti-aging composition 100 may include a partially reduced form of methylene blue as to enhance its ability to cross the BBB while still maintaining its ability to stain, as the leuco format is colorless to light orange/tan.

Anti-aging composition 100 also includes β-nicotinamide mononucleotide 108. "β-nicotinamide mononucleotide" as used in this disclosure is defined a nucleotide derived from ribose, nicotinamide, nicotinamide riboside and niacin. Humans have enzymes that can use (β-nicotinamide mononucleotide (NMN) to generate nicotinamide adenine dinucleotide. Furthermore, NMN is a precursor of nicotinamide adenine dinucleotide (NAD+), a molecule that may be useful in slowing down some aspects of aging. NAD+ serves many critical functions in our cells, such as electron transport, cell signaling, and DNA repair. For anti-aging composition 100, the leucomethylene blue may be combined with the β-nicotinamide mononucleotide via chemical bonds so to construct one unique synthetic molecule, but not to diminish their individual actions or effectiveness. To further enhance this pathway, the attachment of the structure of OAC1 may be performed. "OAC1" (Oct4-activating compound 1) as used in this disclosure is defined as an OCT-4-activating compound that activates expression through the OCT-4 gene promoter. Oct-4 is a transcription factor that is critically involved in the self-renewal of pluripotent stem cells, and its expression is commonly used as a marker for pluripotency. In an embodiment, the addition of OSKM (Oct-3/4, Sox2, Klf4, c-Myc) factors may also enhance various aspects of aging by rejuvenating aging cells and promoting tissue regeneration as described in further detail below. The OSKM factors (Oct-3/4, Sox2, Klf4, c-Myc) are a group of protein transcription factors that may play a vital role in the creation of induced pluripotent stem cells, often called iPSCs. The OSKM factors may also promote expression of non-pluripotency genes and may control how DNA is copied for translation into other proteins. For example, the OSKM factors may promote epigenetic rejuvenation in the pancreas. By way of another example, OCT4 may promote expression of genes important for mouse primitive endodern, Sox2 may promote expression of primitive endoderm genes in mouse blastocysts, Klf4 may regulate expression of promotive endoderm genes in the mouse blastocyst and c-Myc may regulate endodermal genes in fibroblasts and embryonic stem cells. OSKM factors may induce expression of endodermal genes in somatic cells. "Somatic cells" as used in this disclosure are defined as any cell of a living organism other than the reproductive cells. "Pluripotent" as used in this disclosure is defined as (an immature/stem cell) capable of giving rise to several different cell types. For example, many types of cells originate from pluripotent bone marrow stem cells. Reprogramming cells to pluripotency may reverse various age-related cellular phenotypes, including in non-dividing, terminally differentiated cells. The OSKM factors may be highly expressed in embryonic stem cells, and their over-expression may induce pluripotency in human somatic cells. These factors may regulate the developmental signaling network necessary for embryonic stem cell pluripotency and nay be used to transform an adult cell into induced pluripotent stem cells. The combination of leucomethylene blue and NMN (and optionally OAC1) may be called AqLNMNo1 (aqueous leucomethylene blue (β-nicotinamide mononucleotide version 1).

Referring again to FIG. 1, anti-aging composition may also include Trichostatin A 112. "Trichostatin A," as used in this disclosure is defined as an organic compound that serves as an antifungal antibiotic and selectively inhibits the class I and II mammalian histone deacetylase (HDAC) families of enzymes, but not class III HDACs. "Histone deacetylase" (HDAC) is an enzyme that removes the acetyl group from histone proteins on DNA, making the DNA less accessible to transcription factors. Histone deacetylase (HDAC) inhibitors are a relatively new class of anti-cancer agents that play important roles in epigenetic or non-epigenetic regulation, inducing death, apoptosis, and cell cycle arrest in cancer cells. Class I, II and IV HDACs are a group of enzymes that catalyze the removal of acetyl groups from lysine residues in histones and cellular proteins, whereas class III HDACs (Sirt1-Sirt7) form a distinct family of NAD-dependent deacetylases that can be inhibited by nicotinamide. Trichostatin A may be advantageous because it inhibits Class I and II HDACs, but not the Class III HDACs (Sirts). In an embodiment, it may be advantageous to modify the compound AqLNMNo1 to include a subset/addition/molecule to act in reducing the epigenetic barriers to reprogramming, and also potentially improve the efficiency and quality of the derived induced pluripotent stem cells (iPS cells). "Induced pluripotent stem cells" as used in this disclosure are derived from skin or blood cells that have been reprogrammed back into an embryonic-like pluripotent state that enables the development of an unlimited source of any type of human cell needed for therapeutic purposes. For example, iPS cells can be prodded into becoming beta islet cells to treat diabetes, blood cells to create new blood free of cancer cells for a leukemia patient, neurons to treat neurological disorders and the like. By way of another example, iPS cells may also be utilized in treating age-related macular degeneration (AMD). "Age-related macular degeneration" as used in this disclosure is defined as the progressive loss of central vision in the elderly. Pluripotent stem cells may have a broad use in the field of medicine and anti-aging, they may also be utilized in treating, without limitation, spinal cord injuries, heart diseases, osteopetrosis, anemia and the like. In an embodiment, trichostatin A may be combined with compound AqLNMNo1 to make resulting, synthetic and complex, compound AqLNMNo2 (aqueous leucomethylene blue (β-nicotinamide mononucleotide version 2). Trichostatin A 112 may be bound to compound AqLNMNo1 via the hydroxyl group.

Still referring to FIG. 1, composition 100, in another embodiment, vorinostat may be combined with compound AqLNMNo1. "Vorinostat" (also known as suberoylanilide hydroxamic acid) as used in this disclosure is defined as a member of a larger class of compounds that inhibit histone deacetylases (HDAC). Vorinostat (and trichostatin A) are pan-HDAC inhibitors of all zinc-dependent HDACs and may be beneficial because they chelate zinc ions in the active site of histone deacetylases, preventing histone unpacking so DNA is less available for transcription. They may also cross the blood brain barrier and they have shown potential in treating and preventing neurodegenerative diseases, as well as enhancing neuroprotection and neuronal differentiation. "Neurodegenerative disease" as used in this disclosure is defined as a disease which occurs when nerve cells in the brain or peripheral nervous system lose function over time and ultimately die. For example, Alzheimer's disease (AD) and Parkinson's disease (PD) are two common types of neurodegenerative diseases. Alzheimer's disease is thought to be caused by the abnormal build-up of proteins in and around brain cells. One of the proteins involved is called amyloid, deposits of which form plaques around brain cells and the other protein is called tau, deposits of which form tangles within brain cells. In an embodiment, vorinostat may be combined with compound AqLNMNo1 to make resulting, synthetic and complex, compound AqLNMNo2 (aqueous leucomethylene blue (β-nicotinamide mononucleotide version 2).

Still referencing FIG. 1, composition 100 also includes zwitterionic liposomes 116. "Zwitterionic" or "zwitterion" as used in this disclosure is defined as a molecule that contains an equal number of positively and negatively charged functional groups. For example, amino acids are the most common example of zwitterions. They are made up of an ammonium or amino group which contains a positive charge as well as a carboxyl group which contains a negative charge. "Liposome" as used in this disclosure is defined as a minute spherical sac of phospholipid molecules enclosing a water droplet, especially as formed artificially to carry drugs or other substances into the tissues. There are three types of liposomes: MLV (multilamellar vesicles) SUV (small unilamellar vesicles) and LUV (large unilamellar vesicles). For example, there are various way in which industries use liposomes as drug delivery vehicles in medicine, adjuvants in vaccination, signal enhancers/carriers in medical diagnostics and analytical biochemistry, solubilizers for various ingredients as well as support matrices for various ingredients and penetration enhancers in cosmetics. In an embodiment, the addition of zwitterionic liposomes 116 to compound AqLNMNo2 (aqueous leucomethylene blue (β-nicotinamide mononucleotide version 2) helps to assist the AqLNMNo2 to effectively cross the blood brain barrier. The term AqLNMNo3 (aqueous leucomethylene blue β-nicotinamide mononucleotide version 3) may be used to describe this final compound. In an embodiment, a method of hydration and extrusion may be utilized which standardizes the size of the liposomes. For example, one of the simplest ways to prepare liposomes in a research laboratory is the thin-film hydration method followed by extrusion. This method involves making a thin lipid film in a round bottom flask by the removal of organic solvent. Heterogeneous liposomes are formed upon addition and agitation of the dispersion medium. Finally, after extrusion through polycarbonate membranes, homogeneous small liposomes are obtained.

Still referring to FIG. 1, composition 100 may be administered in any suitable manner. In an embodiment, composition 100 may be delivered orally. The composition may be provided to a user in a capsule, tablet, lozenge, troche, suspension, suppository, orally disintegrating tablet, transdermal patch, an inhaled formulation and/or metered dose inhaler. Capsule may include, without limitation, hard-shelled capsules and soft-shelled capsules. Tablets may include, without limitation, solid unit dosage form of medications with suitable excipients and prepared either by molding and/or by compression. Composition 100 may alternatively or additionally be absorbed through a mucous membrane, for instance via aerosolized delivery to the nostrils and/or lungs. Alternatively, or additionally, composition 100 may be administered using a patch, such as without limitation a microneedle patch that delivers lyophilized vaccine in powder form. As a further non-limiting example, composition 100 may be delivered in liquid and/or lyophilized form to any mucous membrane; for instance, and without limitation, composition 100 may be delivered as a lyophilized inhalable powder for absorption in nasal and/or pulmonary surfaces. Composition 100 in lyophilized form may be delivered by a nanobot.

A method for cell reprogramming may include receiving cell reprogramming agents, wherein the reprogramming agents may include Oct-4, Sox 2 and Klf4 (OSK), to reprogram the cell to an embryonic state. In an embodiment, the reprogramming agents may also include c-Myc (OSKM). "Embryonic state" as used in this disclosure is defined as a state where a cell behaves like an embryonic stem cell and where it can become any other cell type in the mammalian body. The method may be applicable to anti-aging and also to treat age-related disease, and even acute injury. "Acute injury" as used in this disclosure is defined as a sudden and often overwhelming injury that results from some kind of severe and sudden physical insult to the body. An acute injury may accelerate the epigenetic clock at the local injury site. An "epigenetic clock" as used in this disclosure is defined as a biochemical test that can be used to measure age. The test may be based on DNA methylation levels, measuring the accumulation of methyl groups to one's DNA molecules. For example, a spinal cord injury site may exhibit advanced DNA methylation changes, which may control regeneration-associated genes (RAG) which control the regeneration capacity and neuronal growth/regrowth or even repair. In an embodiment, cells may be reset from old donors back into a pluripotent state and can become any other cell type in the human body (iPSCs). Once reprogrammed, the cells may demonstrate a higher growth rate than the aged cells they are reprogrammed from, and also may have longer telomeres as well as mitochondria that act in a youthful manner. "Telomeres" as used in this disclosure are defined as a region of repetitive nucleotide sequences associated with specialized proteins at the ends of linear chromosomes. "Mitochondria" as used in this disclosure is defined as an organelle found in large numbers in most cells in which the biochemical processes of respiration and energy production occur. Reprogramming these cells may reverse some of the aspects of aging and may turn the cell's epigenetic clocks back to a similar state as during their original development. Then these iPSC cells may be directed to become the target cell type once again using other reprogramming factors. These reprogrammed cells no longer express the epigenetic patterns correlated with aged cells and demonstrate a gene expression profile consistent with young cells. Additionally, this may also revert mitochondrial function, telomere length and oxidative stress to a state consistent with young cells, as telomere attrition and mitochondrial dysfunction are two other pillars of aging. This may also cause an increase of satellite cells in skeletal muscle, which typically decline during aging.

In an embodiment, cells may be genetically engineered within the patient to express the OSKM factors via, for instance, an antibiotic-activated lentiviral package administered orally or by other means, and the OSKM are transiently expressed for that duration. Once the activator is removed, the OSKM genes may again be silenced. This course may be repeated or vary in duration. In another embodiment, this may be performed outside the patient/donor's body. In another embodiment, other methods may be used to activate/silence the OSKM factors without the need for pre-engineering to respond to the antibiotic-lentiviral package, such as the cell reprogramming composition 100 described above.

Figure 2A:
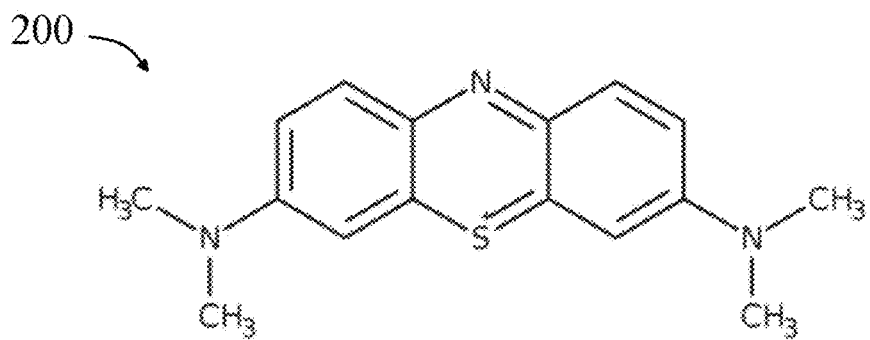
FIGS. 2A-E are diagrams illustrating exemplary chemical structures contained within the anti-aging composition.

Referring now to FIG. 2A, a diagram of at least a chemical structure is illustrated. At least a chemical structure may include methylene blue 200.

Figure 2B:
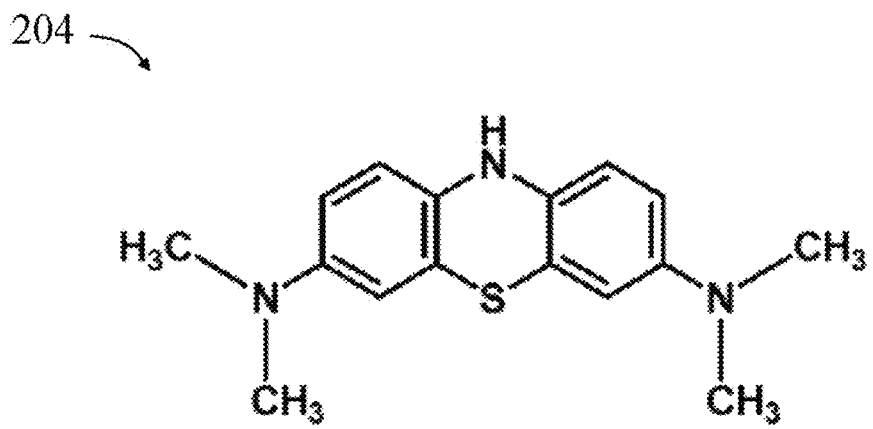

Referring now to FIG. 2B, a diagram of at least a chemical structure is illustrated. At least a chemical structure may include leucomethylene blue 204 (base molecule 104).

Figure 2C:
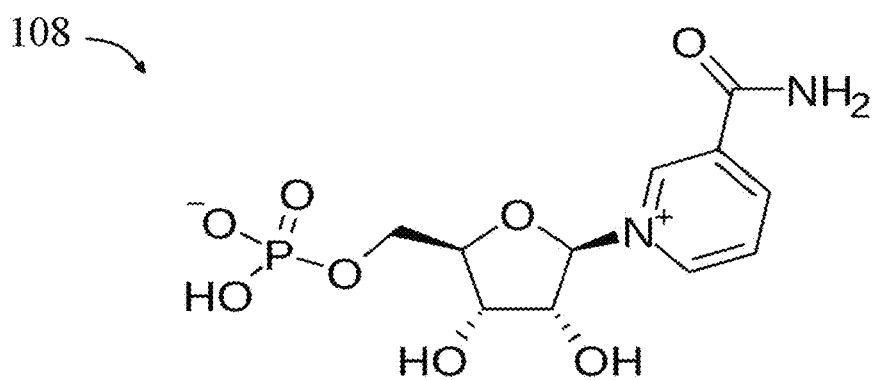

Referring now to FIG. 2C, a diagram of at least a chemical structure is illustrated. At least a chemical structure may include β-nicotinamide mononucleotide 108.

Figure 2D:
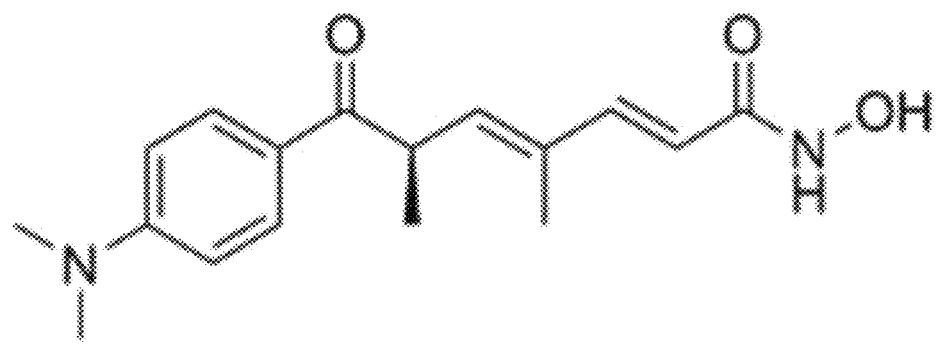

Referring now to FIG. 2D, a diagram of further chemical structures of composition 100 is illustrated. At least a chemical structure may include Trichostatin A 112.

Figure 2E:
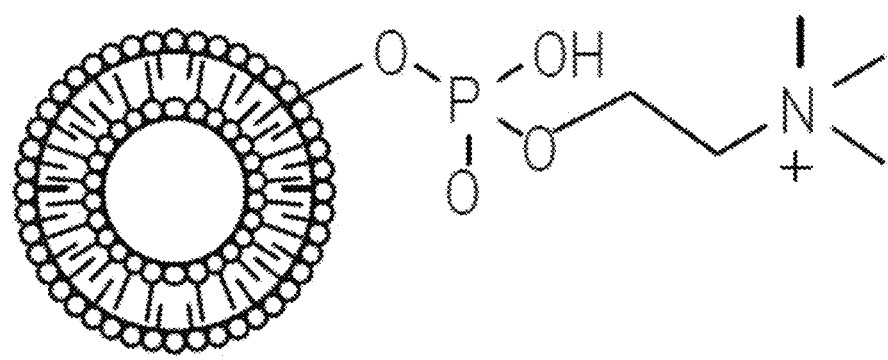

Referring now to FIG. 2E, a diagram of further chemical structures of composition 100 is illustrated. Finally, at least a chemical structure may include zwitterionic liposomes 116.

The anti-aging composition 100 may be customized for immunocompromised users. "Immunocompromised" as used in this disclosure is defined as having an impaired immune system. This may be diagnosed by obtaining immunity health data of the user by, for example, obtaining an analysis of such as the user's blood. For example, a blood test may show the user's white blood cell count. White cells in the blood are an integral part of the human immune system and when a person gets sick the body produces more white blood cells to fight the viruses, bacteria or other pathogens causing the illness, therefore, if a person's white blood cell count is abnormally high this may indicate an immunocompromised condition. Immunity health data may be utilized to determine a degree of immunodeficiency of the user. For example, this may be performed by data classifying a subject to be immunocompromised. A processor and/or computing device may utilize a machine learning processes to conduct the comparison of user and immunity health data inputs. In some embodiments, a machine learning algorithm input may be the plurality of user inputs, wherein the training data may be the inputs of immunity health data, and the algorithm output may be the degree of immunodeficiency.

Additionally, or alternatively, processor and/or computing device may utilize a knowledge-based system (KBS) to compare inputs for compatibility. As used in this disclosure, a KBS is a computer program that reasons and uses a knowledge base to solve complex problems. The KBS has two distinguishing features: a knowledge base and an inference engine. A knowledge base may include technology used to store complex structured and unstructured information used by a computer system, often in some form of subsumption ontology rather than implicitly embedded in procedural code. Other common approaches in addition to a subsumption ontology include frames, conceptual graphs, and logical assertions. In some embodiments, the knowledge base may be a storage hub that contains information about past matches of users to postings based on the similarity of inputs and feedback from users and employers about the compatibility of matches. Next, an Inference engine allows new knowledge to be inferred. For example, the inference engine may determine that a user is associated more often with a high degree of immunodeficiency when the user input includes "White Blood Cell Count"+"C-Reactive Protein Count" rather than just the "White Blood Cell Count" alone. Most commonly, it can take the form of IF-THEN rules coupled with forward chaining or backward chaining approaches. Forward chaining starts with the known facts and asserts new facts. Backward chaining starts with goals and works backward to determine what facts must be asserted so that the goals can be achieved. Other approaches include the use of automated theorem provers, logic programming, blackboard systems, and term rewriting systems such as CHR (Constraint Handling Rules). The inference engine may make predictions or decisions in optimizing classifying postings to a user without being explicitly programmed to do so. The inference engine may receive constant feedback and self-learn based on previous classifications, as described through this disclosure, and recommendations to further refine and strengthen its recommendations.

Processor and/or computing device may be configured to classify the user's degree of immunodeficiency as a function of the comparison. Classifier may include a classification algorithm wherein the algorithm output is a degree of immunodeficiency optimized for the user. In some embodiments, the classification algorithm may take a plurality of user inputs as inputs, wherein the training data includes a plurality of immune health data inputs, data from a KBS, output data of any other classification/comparison described throughout this disclosure, and the like.

Processor and/or computing device, as a function of the comparison, may be configured to rank a plurality of degrees of immunodeficiency in order of similarity to a user immune health data, wherein a rank of degrees of immunodeficiency is based on the similarity score. In some embodiments, generating the ranking may include linear regression techniques. Processor and/or computing device may be designed and configured to create a machine-learning module using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Processor and/or computing device may be configured to use classifier to classify, as a function of ranking, the user to a ranked plurality of degrees of immunodeficiency. In some embodiments, processor and/or computing device may be configured to produce classification output results including the classified ranked postings in a selectable format by user. For example, user may select to output classified ranked postings in a pie chart, wherein the ranked classified postings are divided, and color coded in selectable classification bins. This may be any classifier as described in further detail below.

Processor and/or computing device may be configured to use generative artificial intelligence to analyze cell reprogramming content and data. "Generative artificial intelligence" as used in this disclosure is defined as any type of artificial intelligence system that relies on unsupervised or semi-supervised learning algorithms to create new digital images, video, audio, and text. Through generative artificial intelligence, computers may learn fundamental patterns relevant to input, which may enable them to output similar content. These systems may rely on generative adversarial networks (GANs), variational autoencoders, and transformers. For example, computer-assisted molecular design may be performed and molecular structure generation may be performed by using algorithms for molecule assembly from predefined virtual reactions and reactants.

Any and all determinations described above may be performed and analyzed using an optimization program. Processor may compute a score associated with the threshold and select compliance items to minimize and/or maximize the score, depending on whether an optimal result is represented, respectively, by a minimal and/or maximal score; a mathematical function, described herein as an "objective function," may be used by processor to score each possible pairing. Objective function may be based on one or more objectives as described below. Each factor may be assigned a score based on predetermined variables. In some embodiments, the assigned scores may be weighted or unweighted.

Processor may generate an objective function. An "objective function" as used in this disclosure is a process of minimizing or maximizing one or more values based on a set of constraints. In some embodiments, an objective function may include an optimization criterion. For example, an optimization criterion may be a threshold. An optimization criterion may include any description of a desired value or range of values for one or more attributes; desired value or range of values may include a maximal or minimal value, a range between maximal or minimal values, or an instruction to maximize or minimize an attribute. As a non-limiting example, an optimization criterion may specify that an attribute should be within a 1% difference of an attribute criterion. An optimization criterion may alternatively request that an attribute be greater than a certain value. An optimization criterion may specify one or more tolerances for precision in a matching of attributes to improvement thresholds. An optimization criterion may specify one or more desired attribute criteria for a matching process. In an embodiment, an optimization criterion may assign weights to different attributes or values associated with attributes. One or more weights may be expressions of value to a user of a particular outcome, attribute value, or other facet of a matching process. Optimization criteria may be combined in weighted or unweighted combinations into a function reflecting an overall outcome desired by a user; function may be an attribute function to be minimized and/or maximized. A function may be defined by reference to attribute criteria constraints and/or weighted aggregation thereof as provided by processor; for instance, an attribute function combining optimization criteria may seek to minimize or maximize a function of improvement threshold matching.

Optimizing an objective function may include minimizing a loss function, where a "loss function" is an expression an output of which an optimization algorithm minimizes to generate an optimal result. As a non-limiting example, processor may assign variables relating to a set of parameters, which may correspond to score attributes as described above, calculate an output of mathematical expression using the variables, and select a pairing that produces an output having the lowest size, according to a given definition of "size," of the set of outputs representing each of plurality of candidate improvement thresholds; size may, for instance, included absolute value, numerical size, or the like. Selection of different loss functions may result in identification of different potential pairings as generating minimal outputs. Objectives represented in an objective function and/or loss function may include minimization of differences between attributes and improvement thresholds.

Optimization of objective function may include performing a greedy algorithm process. A "greedy algorithm" is defined as an algorithm that selects locally optimal choices, which may or may not generate a globally optimal solution. For instance, processor may select immune health data so that scores associated therewith are the best score for vaccine schedule considering a user who is immunodeficient.

Objective function may be formulated as a linear objective function, which processor may solve using a linear program such as without limitation a mixed-integer program. A "linear program," as used in this disclosure, is a program that optimizes a linear objective function, given at least immune health data of a user. A mathematical solver may be implemented to solve for the set construction and geographical constraints that maximizes scores; mathematical solver may be implemented on a processor and/or another device, and/or may be implemented on third-party solver.

Optimizing objective function may include minimizing a loss function, where a "loss function" is an expression an output of which an optimization algorithm minimizes to generate an optimal result. As a non-limiting example, processor may assign variables relating to a set of parameters, which may correspond to score components as described above, calculate an output of mathematical expression using the variables, and select a construction constraint that produces an output having the lowest size, according to a given definition of "size," of the set of outputs representing each of plurality of candidate ingredient combinations; size may, for instance, included absolute value, numerical size, or the like. Selection of different loss functions may result in identification of different potential pairings as generating minimal outputs.

Figure 3:
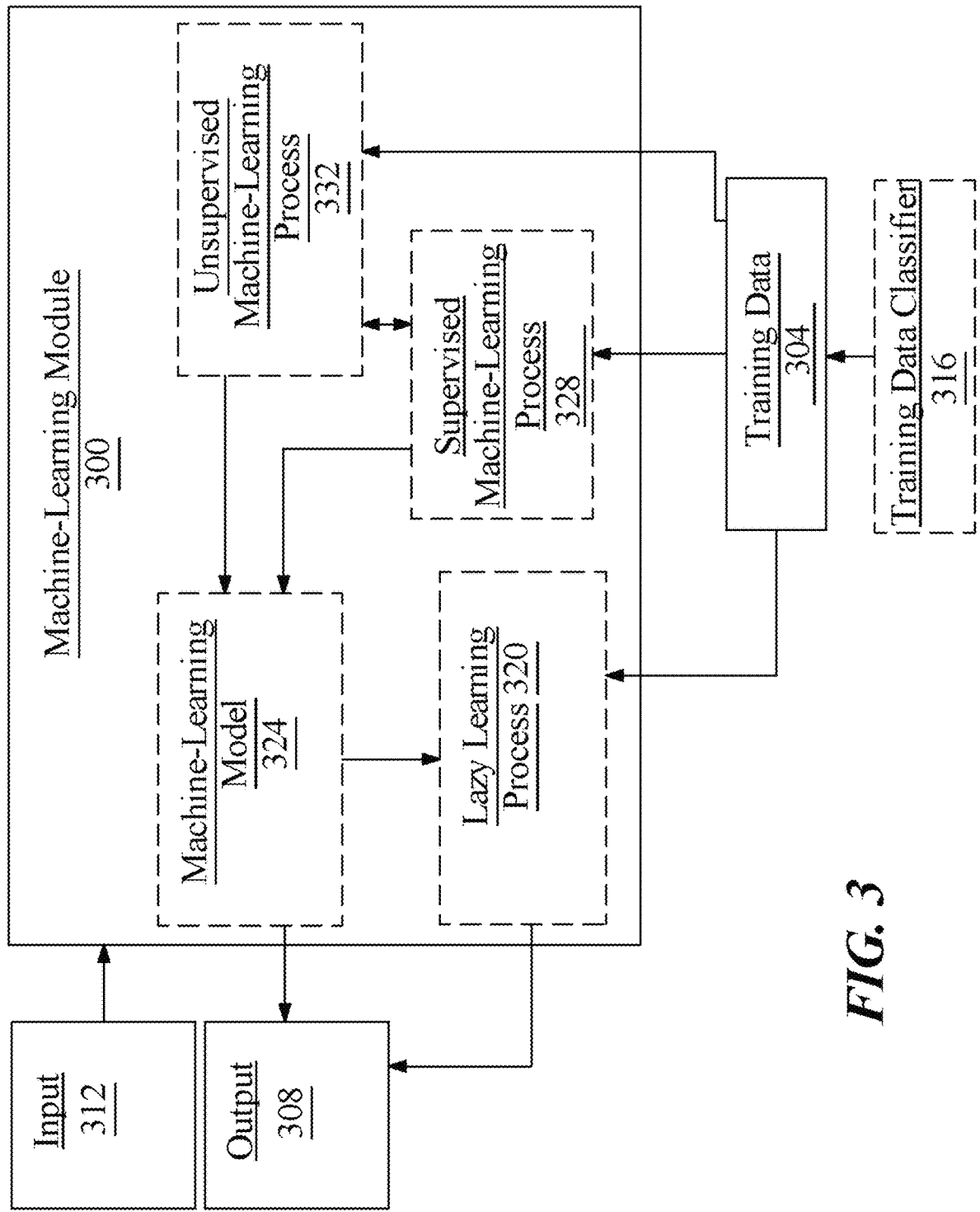
FIG. 3 is a diagram of an exemplary embodiment of a machine-learning module.

Referring now to FIG. 3, a diagram of an exemplary embodiment of a machine-learning module is presented. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatically may enable the same training data 304 to be made applicable for two or more distinct machine-learning algorithms as described in further detail below. Training data 304 used by machine-learning module 300 may correlate any input data as described in this disclosure to any output data as described in this disclosure.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a process whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors' classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively, or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs and outputs as described above in this disclosure, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Fresenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 4:
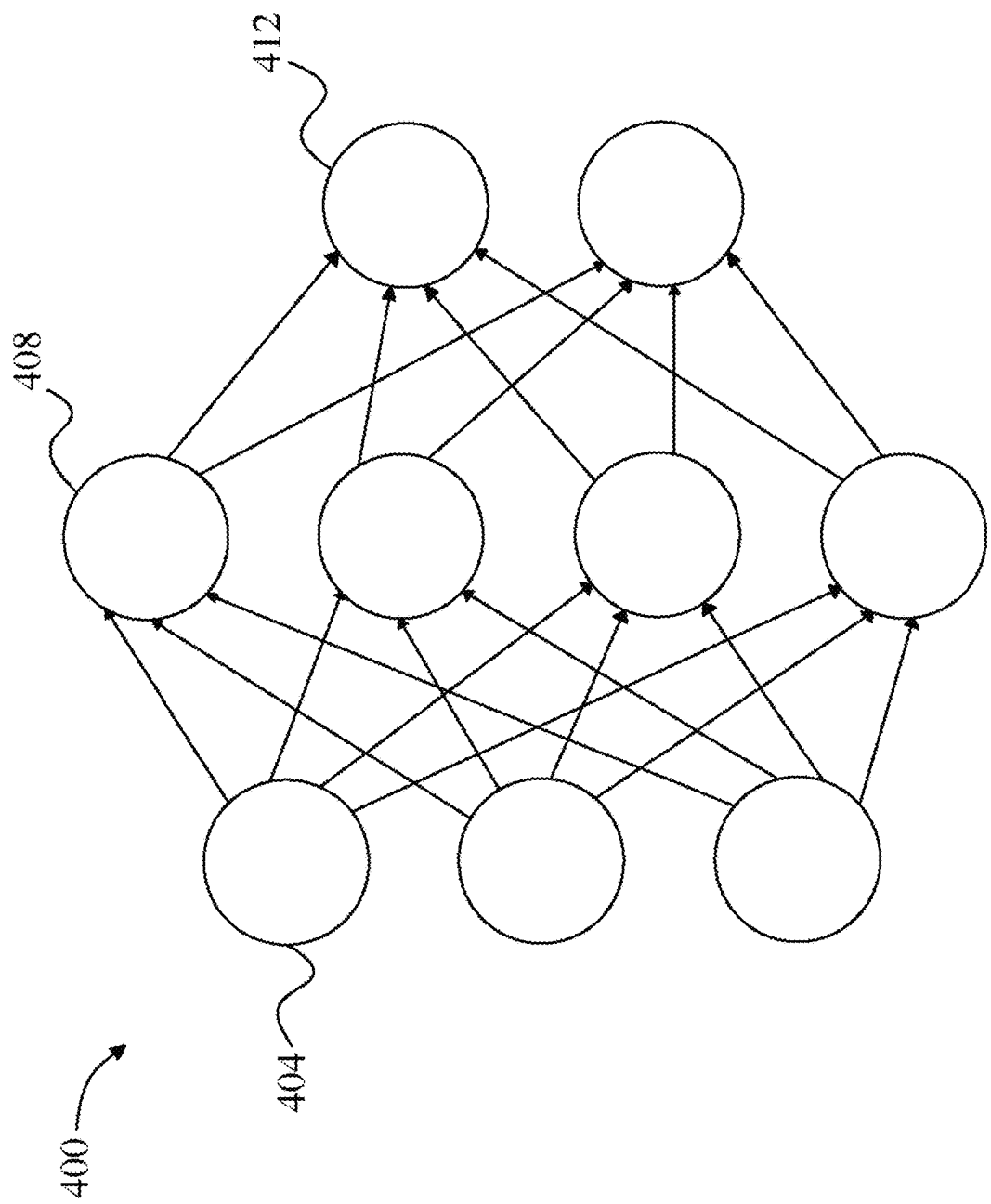
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training"

the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
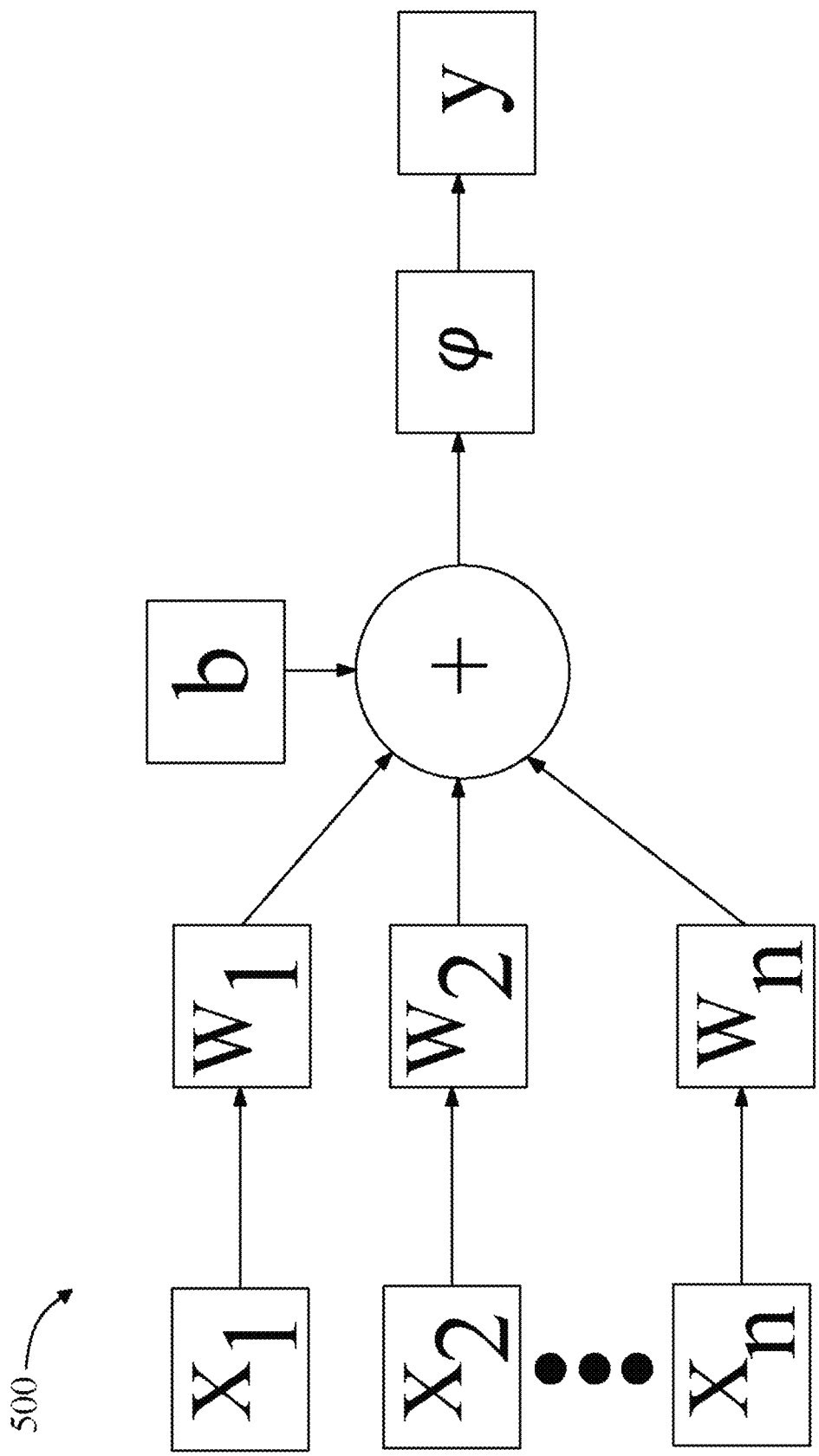
FIG. 5 is a diagram of an exemplary embodiment of a node of a neural network.

Referring now to FIG. 5, an exemplary embodiment 500 of a node of a neural network is illustrated. A node may include, without limitation, a plurality of inputs x; that may receive numerical values from inputs to a neural network containing the node and/or from other nodes. Node may perform a weighted sum of inputs using weights w, that are multiplied by respective inputs xi. Additionally, or alternatively, a bias b may be added to the weighted sum of the inputs such that an offset is added to each unit in the neural network layer that is independent of the input to the layer. The weighted sum may then be input into a function p, which may generate one or more outputs y. Weight w, applied to an input x; may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights w, may be determined by training a neural network using training data, which may be performed using any suitable process as described above.

Figure 6:
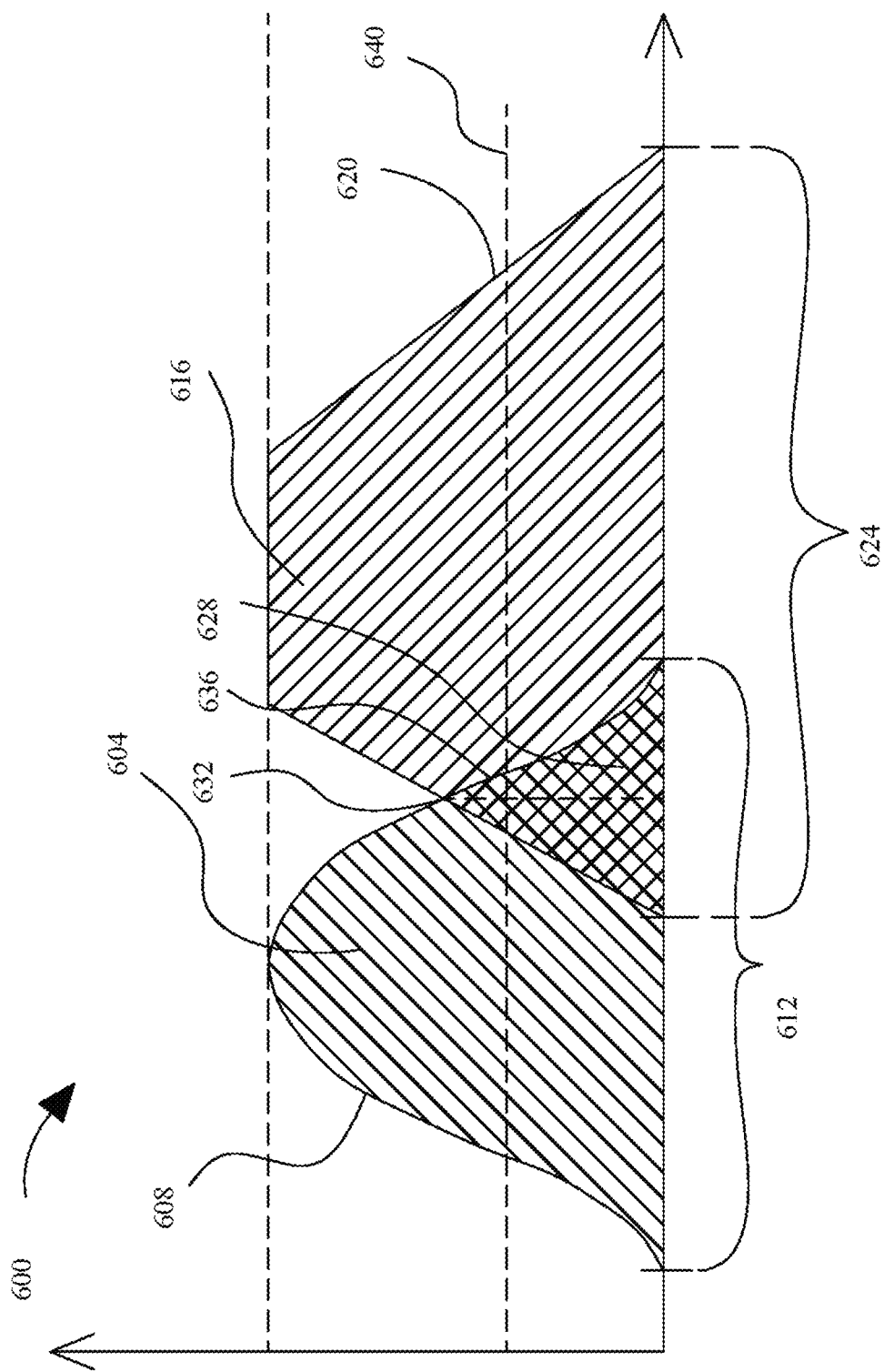
FIG. 6 is a diagram of an exemplary embodiment of a fuzzy set comparison.

Referring to FIG. 6, an exemplary embodiment of fuzzy set comparison 600 is illustrated. A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 804. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \le x < b \\ \frac{c-x}{c-b}, \text{ if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 6, first fuzzy set 604 may represent any value or combination of values as described above, including output from one or more machine-learning models. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 628 that overlaps, first membership function 608 and second membership function 620 may intersect at a point 632 representing a probability, as defined on probability interval, of a match between first fuzzy set 604 and second fuzzy set 616. Alternatively, or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, threshold may indicate a sufficient degree of overlap between an output from one or more machine-learning models and a predetermined class, for combination to occur as described above. Alternatively, or additionally, each threshold may be tuned by a machine-learning and/or statistical process, for instance and without limitation as described in further detail below.

Further referring to FIG. 6, in an embodiment, a degree of match between fuzzy sets may be used to determine a custom vaccine schedule based on input data such as user input data. Where multiple fuzzy matches are performed, degrees of match for each respective fuzzy set may be computed and aggregated through, for instance, addition, averaging, or the like, to determine an overall degree of match.

Still referring to FIG. 6, in an embodiment, custom vaccine schedule may be compared to multiple immune health data fuzzy sets. Machine-learning methods as described throughout may, in a non-limiting example, generate coefficients used in fuzzy set equations as described above, such as without limitation x, c, and σ of a Gaussian set as described above, as outputs of machine-learning methods. Likewise, a custom vaccine schedule may be used indirectly to determine a fuzzy set, as custom vaccine schedule fuzzy set may be derived from outputs of one or more machine-learning models that take the user health data directly or indirectly as inputs.

Still referring to FIG. 6, a computing device may use a logic comparison program, such as, but not limited to, a fuzzy logic model to determine a score. A score may include, but is not limited to, amateur, average, knowledgeable, superior, and the like; each such score may be represented as a value for a linguistic variable representing score, or in other words a fuzzy set as described above that corresponds to a degree of similarity as calculated using any statistical, machine-learning, or other method that may occur to a person skilled in the art upon reviewing the entirety of this disclosure. In other words, a given element of a custom vaccine schedule may have a first non-zero value for membership in a first linguistic variable value and a second non-zero value for membership in a second linguistic variable value. In some embodiments, determining a score may include using a linear regression model. A linear regression model may include a machine learning model. A linear regression model may be configured to map data of design compliance plans to one or more scores. A score classification model may be configured to input collected data and cluster data to a centroid based on, but not limited to, frequency of appearance, and the like. Centroids may include scores assigned to them such that elements of the design plan may each be assigned a score. In some embodiments, and score classification model may include a K-means clustering model. In some embodiments, and score classification model may include a particle swarm optimization model. In some embodiments, determining a score of immunodeficiency may include using a fuzzy inference engine. In some embodiments, a plurality of entity assessment devices may be arranged by a logic comparison program into score arrangements. An "score arrangement" as used in this disclosure is any grouping of objects and/or data based on skill level and/or output score. This step may be implemented as described above in FIGS. 1-5. Membership function coefficients and/or constants as described above may be tuned according to classification and/or clustering algorithms. For instance, and without limitation, a clustering algorithm may determine a Gaussian or other distribution of questions about a centroid corresponding to a given score level, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Further referring to FIG. 6, an inference engine may be implemented according to input and/or output membership functions and/or linguistic variables. For instance, a first linguistic variable may represent a first measurable value pertaining to a degree of similarity, while a second membership function may indicate a degree of similarity of a subject thereof, or another measurable value. Continuing the example, an output linguistic variable may represent, without limitation, a score value. An inference engine may combine rules, such as: "if the difficulty level is 'hard' and the popularity level is 'high', the question score is 'high'"— the degree to which a given input function membership matches a given rule may be determined by a triangular norm or "T-norm" of the rule or output membership function with the input membership function, such as min (a, b), product of a and b, drastic product of a and b, Hamachi product of a and b, or the like, satisfying the rules of commutativity (T(a, b)=T(b, a)), monotonicity: (T(a, b)≤T (c, d) if a≤c and b≤d), (associativity: T(a, T(b, c))=T(T(a, b), c)), and the requirement that the number 1 acts as an identity element. Combinations of rules ("and" or "or" combination of rule membership determinations) may be performed using any T-conorm, as represented by an inverted T symbol or "⊥," such as max (a, b), probabilistic sum of a and b (a|b*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively, or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively, or additionally, output rules may be replaced with functions according to the Takagi-Sugano-King (TSK) fuzzy model.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
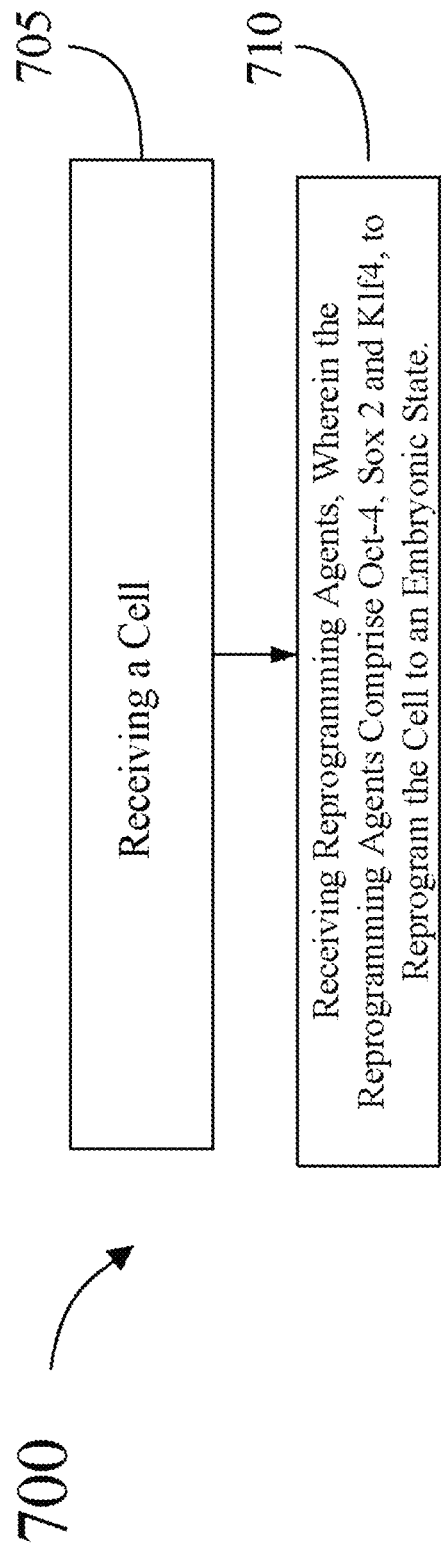
FIG. 7 is a block diagram illustrating an exemplary method of manufacturing a reprogrammed cell.

Referring now to FIG. 7, a method 700 of manufacturing a reprogrammed cell is presented. At step 705, method 700 includes receiving a cell. This step may be implemented as described above in FIGS. 1-6, without limitation. The cell may include a somatic, human cell and the reprogrammed cell may be pluripotent.

Still referring to FIG. 7, at step 710, method 700 includes receiving reprogramming agents, wherein the reprogramming agents may include Oct-4, Sox 2 and Klf4, to reprogram the cell to an embryonic state. This step may be implemented as described above in FIGS. 1-6, without limitation. The reprogramming agents may comprise c-Myc and the reprogramming agents may be introduced to a user by a vector. The vector may include an antibiotic activated lentiviral package and is configured to be administered orally to a user. The Oct-4, Sox 2, Klf4, c-Myc (OSKM) factors may be transiently expressed for the duration of the antibiotic activated lentiviral package and the Oct-4, Sox 2, Klf4, c-Myc (OSKM) factors may be silenced when the antibiotic lentiviral package is removed.

Figure 8:
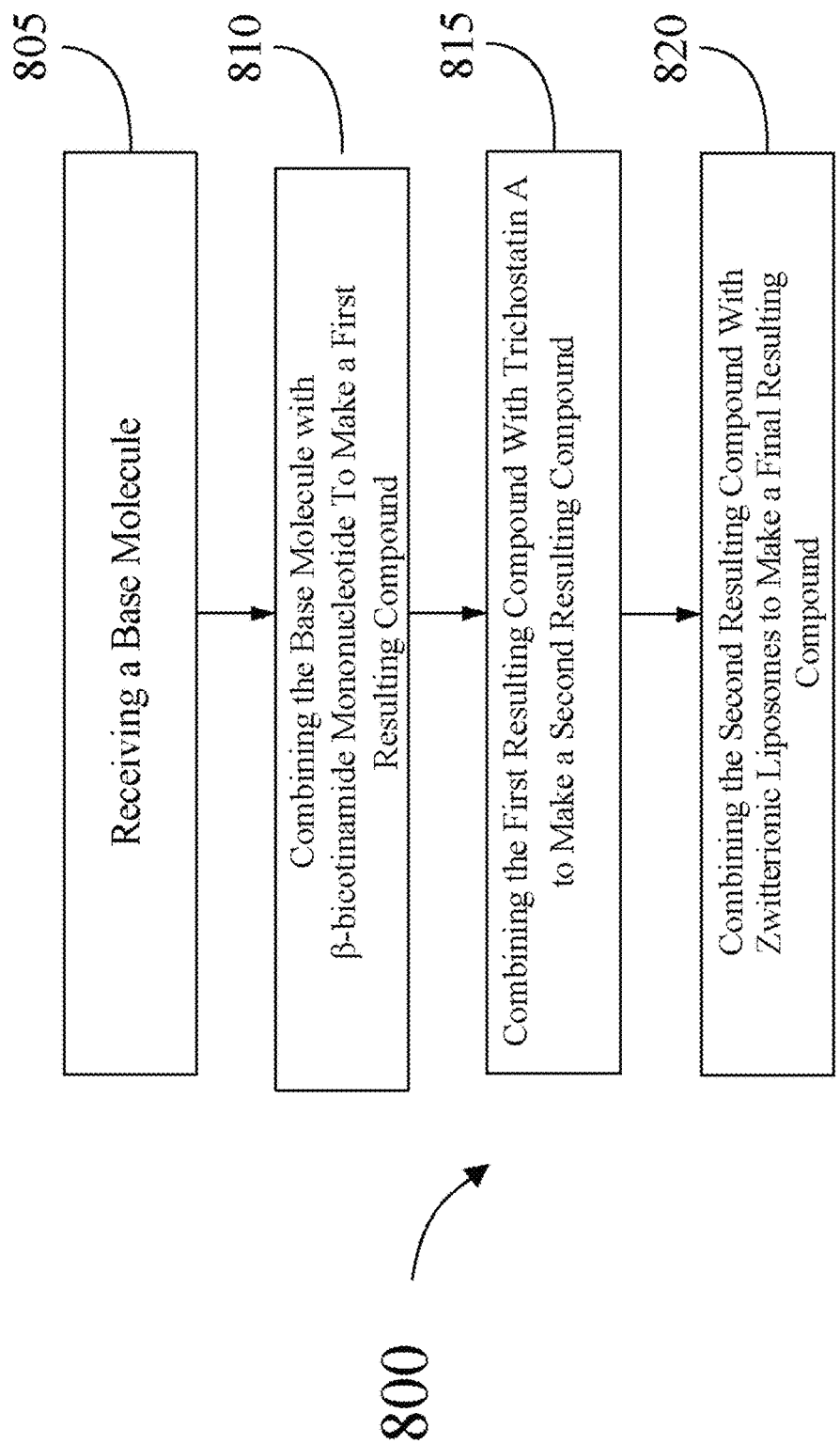
FIG. 8 is a block diagram illustrating another exemplary method for cell reprogramming.

Referring now to FIG. 8, a method 800 of cell reprogramming is presented. At step 805, method 800 includes receiving a base molecule. This step may be implemented as described above in FIGS. 1-7, without limitation.

Still referring to FIG. 8, at step 810, method 800 includes combining an oligonucleotide-based adjuvant with the autologous cell medium. This step may be implemented as described above in FIGS. 1-7, without limitation.

Still referring to FIG. 8, at step 815, method 800 includes combining an antigen with the autologous cell medium and oligonucleotide-based adjuvant. This step may be implemented as described above in FIGS. 1-7, without limitation.

Figure 9:
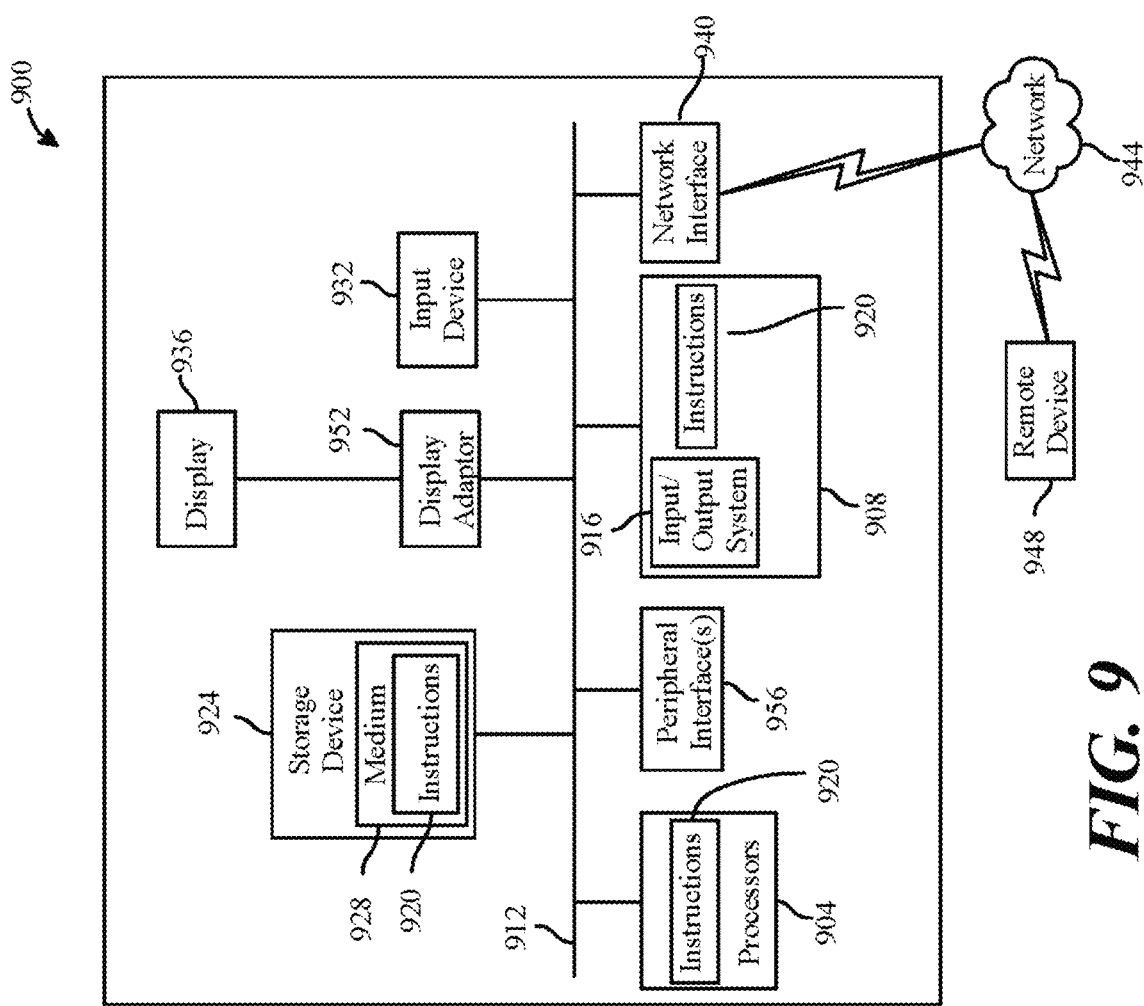
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components hereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956.

Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and systems according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A composition comprising:
   a base molecule;
   a combination of nicotinamide mononucleotide and leucomethylene blue, wherein the combination comprises aqueous leucomethylene blue-nicotinamide mononucleotide version 1 (AqLNMNo1);
   a combination of trichostatin A and aqueous leucomethylene blue-nicotinamide mononucleotide version 1, wherein the combination comprises aqueous leucomethylene blue-nicotinamide mononucleotide version 2 (AqLNMNo2); and
   zwitterionic liposomes.

2. The composition of claim 1, wherein the base molecule comprises partially reduced methylene blue.

3. The composition of claim 1, wherein the base molecule and the (3-nicotinamide mononucleotide are bonded together by chemical bonds.

4. The composition of claim 1, wherein the composition further comprises an octamer activating compound 1 (OAC1).

5. The composition of claim 1, wherein the trichostatin A is combined with the AqLNMNo1 by way of a hydroxyl group.

6. The composition of claim 2, wherein AqLNMNo1 the partially reduced methylene blue, and AqLNMNo2 comprises a synthetic molecule.

7. The composition of claim 1, wherein the composition further comprises vorinostat, wherein the vorinostat is combined with the AqLNMNo1 by way of a hydroxyl group.

8. The composition of claim 1, wherein the zwitterionic liposomes are hydrated and extruded.

9. The composition of claim 1, wherein the composition is configured to be suitable for oral administration.

10. The composition of claim 1, wherein the zwitterionic liposomes comprise amino acids.

* * * * *